United States Patent
Tally

(10) Patent No.: US 9,326,777 B2
(45) Date of Patent: May 3, 2016

(54) DECORTICATING SURGICAL INSTRUMENTS AND GUIDANCE SYSTEMS WITH TACTILE FEEDBACK

(71) Applicant: Amendia, Inc., Marietta, GA (US)

(72) Inventor: William C. Tally, Athens, GA (US)

(73) Assignee: Amendia, Inc., Marietta, GA (US)

( * ) Notice: Subject to any disclaimer, the term of this patent is extended or adjusted under 35 U.S.C. 154(b) by 275 days.

(21) Appl. No.: 14/161,335

(22) Filed: Jan. 22, 2014

(65) Prior Publication Data

US 2014/0276835 A1  Sep. 18, 2014

Related U.S. Application Data

(60) Provisional application No. 61/782,927, filed on Mar. 14, 2013.

(51) Int. Cl.
*A61B 17/16* (2006.01)
*A61B 17/84* (2006.01)

(52) U.S. Cl.
CPC ......... *A61B 17/1604* (2013.01); *A61B 17/1671* (2013.01); *A61B 17/848* (2013.01)

(58) Field of Classification Search
CPC ............... A61B 17/16; A61B 17/1635; A61B 17/1671; A61B 17/1604
USPC ............................................ 606/79–85, 86 R
See application file for complete search history.

(56) References Cited

U.S. PATENT DOCUMENTS

| | | | |
|---|---|---|---|
| 6,110,175 A * | 8/2000 | Scholl ............... | A61B 17/1604 606/79 |
| 8,070,750 B2 * | 12/2011 | Wenstrom, Jr. .... | A61B 17/1604 606/79 |
| 2006/0106394 A1 * | 5/2006 | Colleran ............ | A61B 17/1735 606/86 R |
| 2012/0232658 A1 * | 9/2012 | Morgenstern Lopez ............... | A61B 17/1757 623/17.16 |

* cited by examiner

*Primary Examiner* — Christopher Beccia
(74) *Attorney, Agent, or Firm* — David L. King

(57) ABSTRACT

An instrument for selectively decorticating a bony surface is described. The instrument may have a decorticating implement having a truncated scoop on its medial face and an inclined blade disposed on its opposing lateral face. The blade edge may be coincident with the linear distal edge of the truncated scoop. Also described is a method for using such an instrument to selectively decorticate a bony surface in order to prepare it for service as a bone graft bed.

10 Claims, 6 Drawing Sheets

DECORTICATING SURGICAL INSTRUMENTS AND GUIDANCE SYSTEMS WITH TACTILE FEEDBACK

CONTINUITY

This application claims priority to and the benefit of U.S. Provisional Application No. 61/782,927 filed on Mar. 14, 2013 and which is incorporated herein in its entirety.

BACKGROUND

1. Field of the Disclosure

The following disclosure relates generally to medical devices, systems and methods, including medical instruments for use in performing spinal bone fusion. More specifically, the disclosure relates to a decorticating instrument and a method and system for guiding the instrument to a desired location.

2. Background

Surgical intervention is sometimes required in order to repair or provide additional structural support along the spinal column in cases where a portion of the patient's intervertebral anatomy has become weakened, diseased, or destroyed. Such support systems are also commonly used following a discectomy, where an intervertebral disc is surgically removed.

Posterior lumbar interbody fusion is open-back surgery used to alleviate the symptoms associated with impinged or irritated nerve tissue in the lower (lumbar) back. From an entry point in the back (posterior), the affected vertebrae are permanently connected, or fused, using a bone graft in order to mitigate the instability caused by a spinal condition such as degenerative disc disease.

Patients who undergo this type of lumbar fusion can expect the following:

a. A three- to six-inch incision is made along the lower back, usually parallel with the lumbar spine.

b. The laminae, the spinous process, and a portion of the facet joints are removed from the vertebra to allow access to the intervertebral disc.

c. The damaged or diseased portion of the disc is removed (called a discectomy), but a section of the fibrous disc wall is left intact to aid in bone graft containment.

d. Bone grafts are inserted into the area vacated by the disc; morselized or granular bone might be added to fill the area.

e. Metal screws are attached to the pedicles of the adjacent vertebrae, and rods are inserted through the screws to hold the vertebrae in place.

f. The bone graft grows over time, forming a bridge or fusion between the vertebrae.

In other minimally invasive approaches, percutaneous screws are employed but the procedure does not involve fusion, merely stabilization.

In addition to fixation or stabilization of the joint, it is beneficial to try to stimulate bone growth between the adjacent vertebrae. To do so, spine surgeons use bone graft material in addition to fixation devices. Bone graft doesn't heal or fuse the spine immediately; instead, bone graft provides a foundation or scaffold for the patient's body to grow new bone. Bone graft can stimulate new bone production. When new bone grows and solidifies, fusion occurs. Although instrumentation (e.g., screws, rods) is often used for initial stabilization (post-operative), it is the healing of bone that welds vertebrae together to create long-term stability. There are two general types of bone grafts: real bone and bone graft substitutes. Real bone can come from the patient (autograft) or from a donor bone (allograft). Also used in these types of surgery are bone substitute, osteoinductive agent, and bone cement.

There is a need for improved systems and methods for lumbar interbody fusion.

SUMMARY

Described herein is an instrument for selectively decorticating a bony surface in order to prepare it for use as a bone graft bed. According to particular embodiments, the instrument comprises a shaft extending lengthwise along a longitudinal axis from a proximal handle toward a distal end, and a decorticating implement disposed upon the shaft, wherein the implement has a medial face and a generally opposing lateral face. The implement, according to particular embodiments, comprises (a) a truncated scoop disposed on the medial face, the scoop comprising a generally shallow bowl terminating along a linear distal edge, the scoop defining a semi-cylindrical groove positioned substantially parallel to the longitudinal axis, wherein the groove is sized and shaped to releasably receive a guide wire; (b) an inclined blade disposed on the lateral face, the blade tapering in shape from a first thickness toward the linear distal edge to form a blade edge coincident with the linear distal edge; and (c) a distal notch positioned near the center of the linear distal edge, wherein the notch is sized and shaped to releasably receive the guide wire.

Also described herein is a method of selectively decorticating a bony surface in a bone fusion procedure. The procedure may include percutaneously accessing a desired motion segment of the spine, wherein the desired motion segment comprises a first vertebral body and an adjacent second vertebral body. According to particular embodiments, the method comprises the steps of: (a) inserting a guide wire percutaneously and anchoring the guide wire near the bony surface; (b) sliding a decorticating instrument along the guide wire toward the bony surface, wherein the instrument provides tactile feedback about the location of the instrument relative to the guide wire; and (c) manipulating the decorticating instrument against the bony surface in order to selectively decorticate it and otherwise prepare it for use as a bone graft bed.

Related methods of operation are also provided. Other apparatuses, methods, systems, features, and advantages of the laminoplasty plates and the method of their use will be or become apparent to one with skill in the art upon examination of the following figures and detailed description. It is intended that all such additional apparatuses, methods, systems, features, and advantages be included within this description, be within the scope of the laminoplasty plates and the method of their use, and be protected by the accompanying claims.

BRIEF DESCRIPTION OF THE DRAWINGS

These and other features of the preferred embodiments of the present invention will become more apparent in the detailed description in which reference is made to the appended drawings wherein.

DETAILED DESCRIPTION

Figure 1:
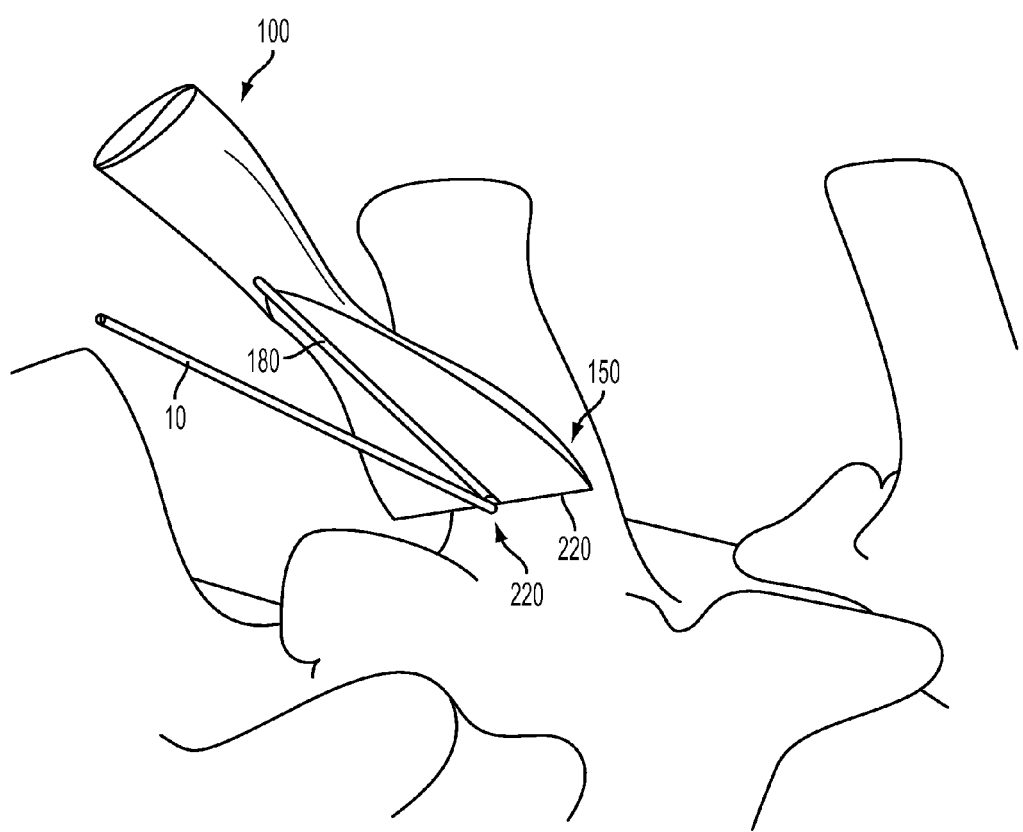
FIG. 1 is a perspective view of a decorticating instrument positioned against a guide wire, according to various aspects.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "screw" includes aspects having two or more screws unless the context clearly indicates otherwise. Also, the words "proximal" and "distal" are used to describe items or portions of items that are situated closer to and away from, respectively, a user or operator such as a surgeon. Thus, for example, the tip or free end of a device may be referred to as the distal end, whereas the generally opposing end or handle may be referred to as the proximal end.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where the event or circumstance occurs and instances where it does not.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

In one exemplified aspect, an instrument for decorticating a bony surface can comprise an elongate shaft having a handle at one end and a decorticating implement at the other. In another aspect, the shaft extends lengthwise along a longitudinal axis. The shaft may be generally cylindrical in overall shape; circular or oval in cross-section. The shaft may include a handle portion at or near the proximal end. The decorticating implement may be disposed on the shaft at or near the distal end. According to particular embodiments, the instrument may also include a tapered body between the shaft and the implement.

FIG. 2 includes a series of orthogonal views of a decorticating instrument, according to particular embodiments. FIG. 2(d) shows an instrument 100 having a proximal handle 120, a shaft 130, a tapered body 140, and a decorticating implement 300 located at the distal end of the instrument.

Figure 2A:
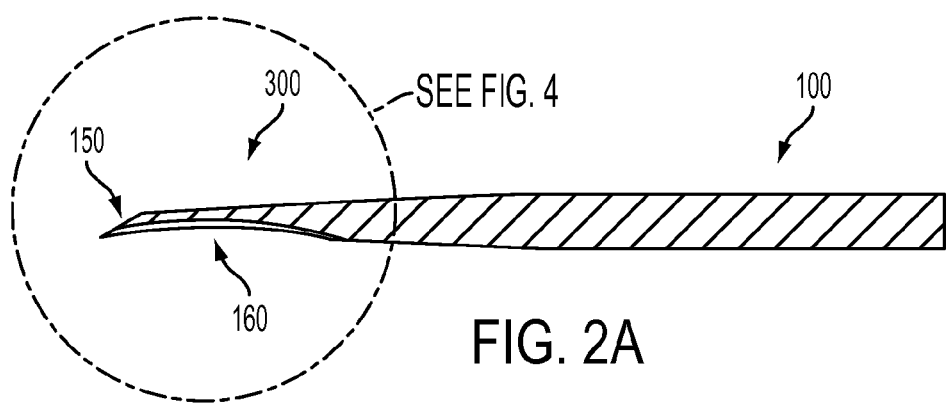
FIG. 2 includes a series of orthogonal views, (a) through (d), of a decorticating instrument, according to various embodiments.
Figure 2B:
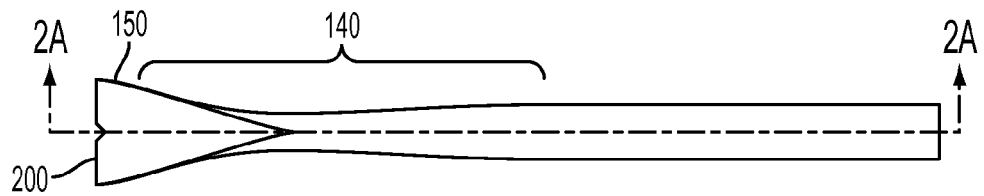
Figure 2C:
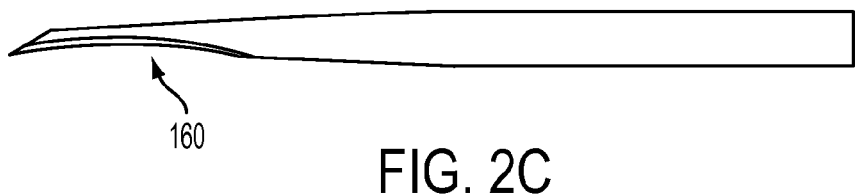
Figure 2D:
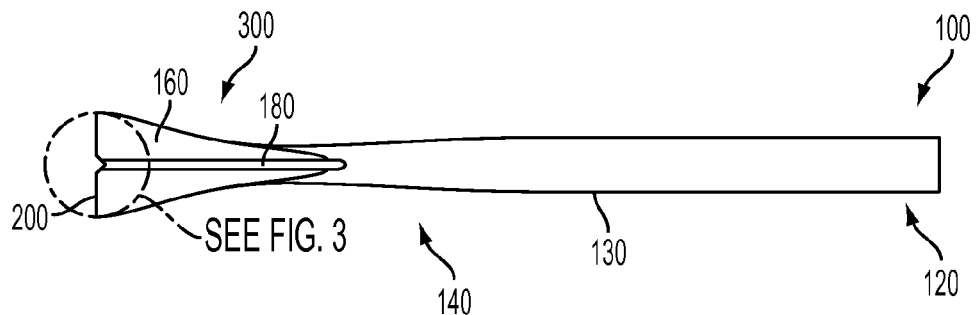

As shown in FIG. 2(a), the implement 300 may include a truncated scoop 160 on one side and an inclined blade 150 on the opposing side. In one aspect, the implement 300 may have a medial face, as shown in FIG. 2(d), and a generally opposing lateral face, as shown in FIG. 2(b). As shown in the FIG. 2(b), according to particular embodiments, both the inclined blade 150 and the truncated scoop 160 terminates along the same, substantially linear, distal edge 200 to form a blade edge.

Figure 3:
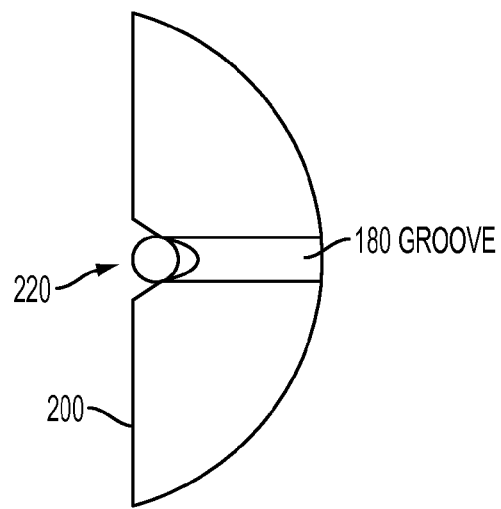
FIG. 3 is a detailed view of the distal end of a decorticating instrument, labeled as area "A" on FIG. 2(d), according to various embodiments.

The truncated scoop 160, as shown in FIG. 2(d), may include a generally shallow bowl terminating along a linear distal edge 200. Along the bowl of the scoop 160, as shown, is a generally semi-cylindrical groove 180 that is oriented generally parallel to the longitudinal axis of the instrument 100. The groove 180 may be sized and shaped to releasably receive a guide wire, such as a 1.4-millimeter Kirschner wire (K-wire). As shown in FIG. 3, the groove 180 may have a diameter, for example, of 0.06 inches. The groove 180 may also be sized and shaped to guide or otherwise assist in moving bone graft material along the bowl of the scoop 160 and toward a selected bone graft bed.

The bowl of the scoop 160 may be shallow relative to the overall size of the shaft. For example, in the embodiment illustrated in FIG. 4, the scoop 160 has an effective radius of 3.29 inches.

The medial face, shown in FIG. 2(d), shows a scoop 160 that is generally triangular in shape, with curvilinear sides, according to particular embodiments. In this aspect, the scoop 160 may appear to be generally wedge-shaped.

The groove 180 may extend along all or part of the bowl of the truncated scoop 160 and, in particular embodiments, may extend proximally beyond the scoop 160 and onto the tapered body 140 and/or onto the shaft 130 of the instrument 100. In the embodiment illustrated in FIG. 2(d), the groove 180 has a length of 1.68 inches.

At the distal end, the groove 180 may extend into and through the linear distal edge 200. According to particular embodiments, the implement 300 may further include a distal notch 220 positioned near the center of the linear distal edge 200, as shown in FIG. 2(*d*) and, in more detail, in FIG. 3. The distal notch 220 may also be sized and shaped to releasably receive a guide wire, such as a Kirschner wire (K-wire). As shown in FIG. 3, the notch 220 may have an effective diameter, for example, of 0.06 inches in order to effectively engage with a 1.4-millimeter guide wire. As shown, the notch 220 may be generally V-shaped. For example, the notch 220 may be 0.11 inches wide at the opening, 0.10 inches deep (plus or minus 0.02 inches), and each side may be inclined at an acute angle (thirty degrees, for example) relative to the longitudinal axis of the instrument 100, as shown in FIG. 3. The groove 180 may extend into and through the distal notch 220, as shown in FIG. 2(*d*) and FIG. 3.

The groove 180, when positioned along a guide wire, provides tactile feedback to the user about the location of the instrument 100 relative to the guide wire. In use, as the user's hand manipulates the instrument 100 and places the groove 180 along a guide wire, the user will receive tactile feedback, through the hand, to indicate whether the groove 180 has been successfully placed against or is otherwise engaged with the guide wire.

Similarly, the distal notch 220, when positioned along a guide wire, also provides tactile feedback to the user about the location of the instrument 100 relative to the guide wire.

Figure 4:
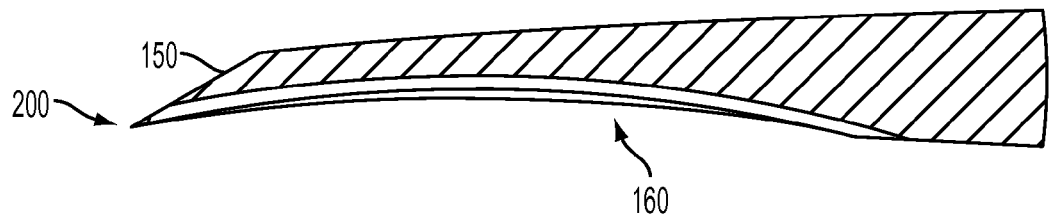
FIG. 4 is a detailed view of the distal end of a decorticating instrument, marked as area "C" on FIG. 2(a), according to various embodiments.

The inclined blade 150, as shown in FIG. 4, may be tapered in overall shape from a first thickness toward the linear distal edge 200 to form a blade edge. The blade 150 may be inclined at an acute angle (thirty degrees, for example) toward the medial face, relative to the longitudinal axis of the instrument 100, as shown in FIG. 2(*c*).

The inclined blade 150 may be positioned on the lateral face of the implement 300, as shown in FIG. 2(*b*). As shown, the inclined portion of the blade 150 may be generally rhomboidal in shape. Also, the blade 150 may extend from the tapered body 140, as shown, and may include one or more additional tapered surfaces. In this aspect, the inclined blade 150 may appear to be generally wedge-shaped.

The blade edge, positioned along and coincident with the linear distal edge 200, may include a distal notch 220 near its center, as shown in FIG. 2(*d*) and, in more detail, in FIG. 3.

As described above, and illustrated in FIG. 4, the truncated scoop 160 also terminates along the distal edge 200. In this aspect, the scoop 160 and the blade 150 may cooperate during use, as described herein. For example, the blade 150 may be pushed in a lateral direction, away from the guide wire, along a bony surface, in order to selectively decorticate the bony surface. Then, the scoop 160 may be pulled in a medial direction, back toward the guide wire, along the bony surface, in order to further decorticate the bony surface. This back-and-forth motion may facilitate the selective decortication of a bony surface—with the guide wire serving as a tactile reference point for the user. For example, as the medial face of the scoop 160 travels back toward the guide wire, the semi-circular groove 180 and/or the distal notch 200 may partially engage with the guide wire, providing a tactile signal to the user when the implement 300 is positioned near the guide wire.

Figure 8:
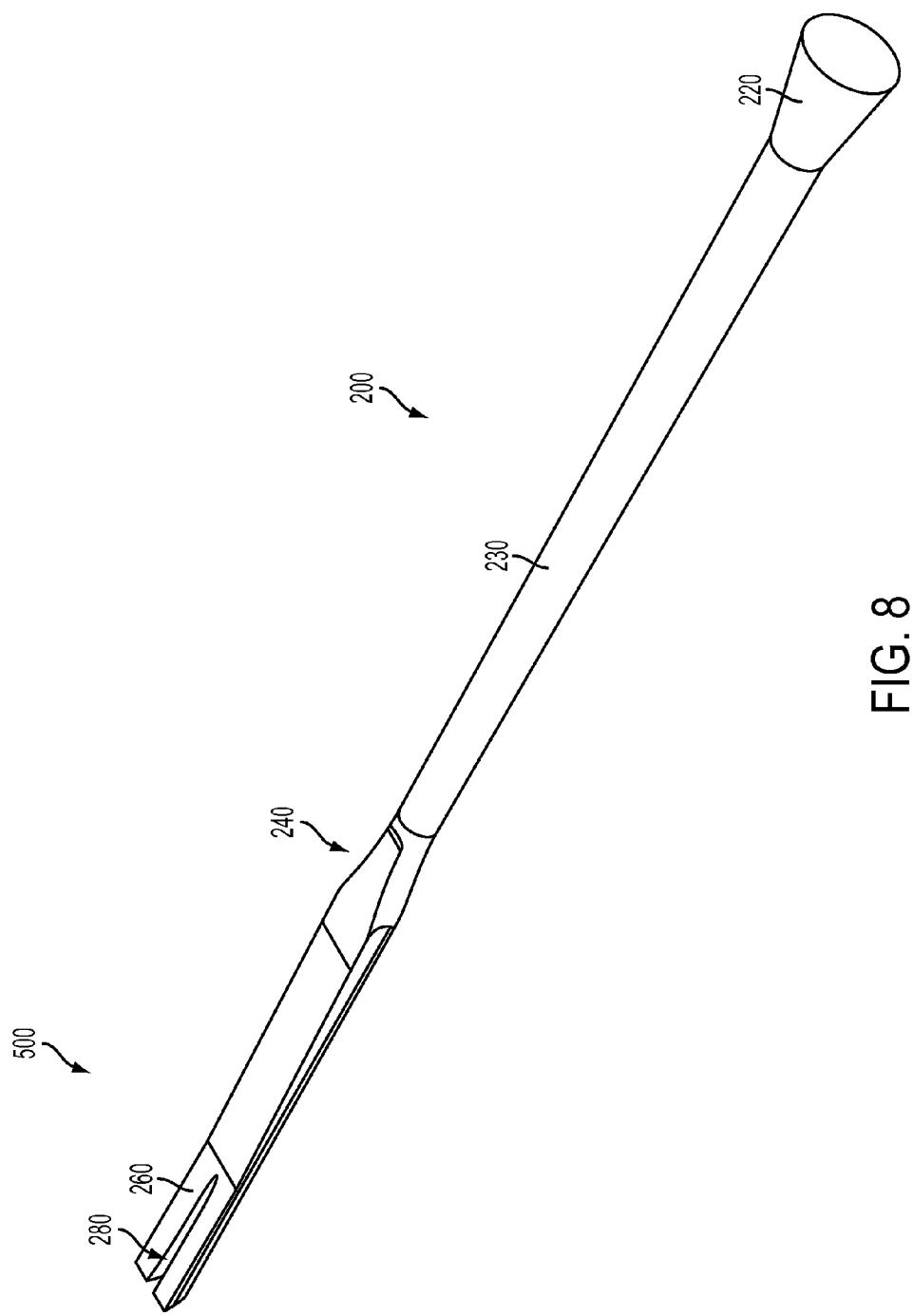
FIG. 8 is a perspective view of a perspective view of a decorticating instrument, according to various embodiments.

FIG. 8 is a perspective view of a decorticating instrument, according to particular embodiments. FIG. 8 shows an instrument 200 having a proximal handle 220, a shaft 230, a tapered body 240, and a decorticating implement 500 located at the distal end of the instrument.

Figure 5:
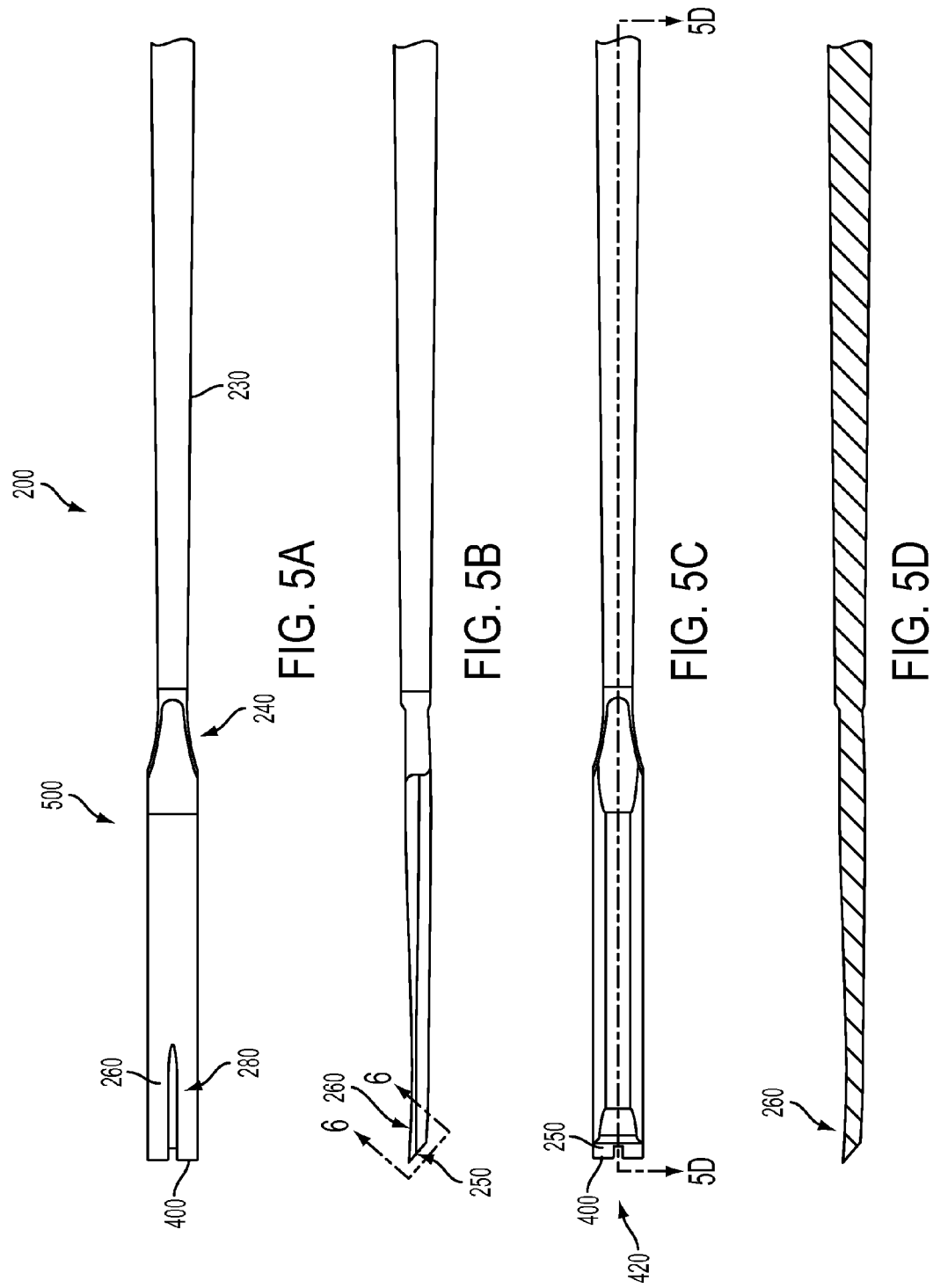
FIG. 5 includes a series of orthogonal views, (a) through (d), of a decorticating instrument, according to various embodiments.

FIG. 5 includes a series of orthogonal views of a decorticating instrument, according to particular embodiments. FIG. 5(*a*) shows an instrument 200 having a proximal handle, a shaft 230, a tapered body 240, and a decorticating implement 500 located at the distal end of the instrument.

As shown in FIG. 5(*b*), the implement 500 may include a truncated scoop 260 on one side and an inclined blade 250 on the opposing side. In one aspect, the implement 500 may have a medial face, as shown in FIG. 5(*a*), and a generally opposing lateral face, as shown in FIG. 5(*c*). As shown in the FIG. 5(*c*), according to particular embodiments, both the inclined blade 250 and the truncated scoop 260 terminates along the same, substantially linear, distal edge 400 to form a blade edge.

The truncated scoop 260, as shown in FIG. 5(*a*), may include a generally shallow bowl terminating along a linear distal edge 400. Along the bowl of the scoop 260, as shown, is a generally semi-cylindrical groove 280 that is oriented generally parallel to the longitudinal axis of the instrument 200. The groove 280 may be sized and shaped to releasably receive a guide wire, such as a 1.4-millimeter Kirschner wire (K-wire). The groove 280 may be sized and shaped to guide or otherwise assist in moving bone graft material along the bowl of the scoop 260 and toward a selected bone graft bed.

The bowl of the scoop 260 may be shallow relative to the overall size of the shaft, as shown in FIG. 5(*d*).

The medial face, shown in FIG. 5(*a*), shows a scoop 260 that is generally rectangular in shape, with linear sides, according to particular embodiments. In the embodiment illustrated in FIG. 5(*a*), the scoop 260 has a width of 0.400 inches.

The groove 280 may extend along all or part of the bowl of the truncated scoop 260 and, in particular embodiments, may extend proximally beyond the scoop 260 and onto the tapered body 240 and/or onto the shaft 230 of the instrument 100. In the embodiment illustrated in FIG. 5(*a*), the groove 280 has a length of 0.919 inches.

Figure 6:
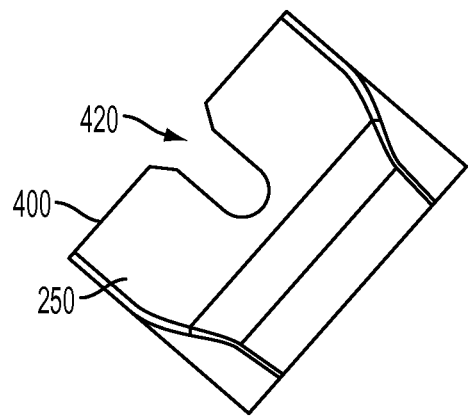
FIG. 6 is a detailed view of the distal end of a decorticating instrument, labeled as section "A-A" on FIG. 5(b), according to various embodiments.

At the distal end, the groove 280 may extend into and through the linear distal edge 400. According to particular embodiments, the implement 500 may further include a distal notch 420 positioned near the center of the linear distal edge 400, as shown in FIGS. 5(*a*) and 5(*c*) and, in more detail, in FIG. 6. The distal notch 420 may also be sized and shaped to releasably receive a guide wire, such as a Kirschner wire (K-wire). As shown in FIG. 6, the notch 420 may have an effective radius, for example, of 0.0335 inches in order to effectively engage with a 1.4-millimeter guide wire. As shown, the opening to the notch 420 may be generally V-shaped. For example, the notch 420 may be 0.100 inches deep and each side of the opening may be inclined at an acute angle (thirty degrees, for example) relative to the longitudinal axis of the instrument 200, as shown in FIG. 6. The groove 280 may extend into and through the distal notch 420, as shown in FIG. 5(*a*).

The groove 280, when positioned along a guide wire, provides tactile feedback to the user about the location of the instrument 200 relative to the guide wire. In use, as the user's hand manipulates the instrument 200 and places the groove 280 along a guide wire, the user will receive tactile feedback, through the hand, to indicate whether the groove 280 has been successfully placed against or is otherwise engaged with the guide wire.

Similarly, the distal notch 420, when positioned along a guide wire, also provides tactile feedback to the user about the location of the instrument 200 relative to the guide wire.

Figure 7:
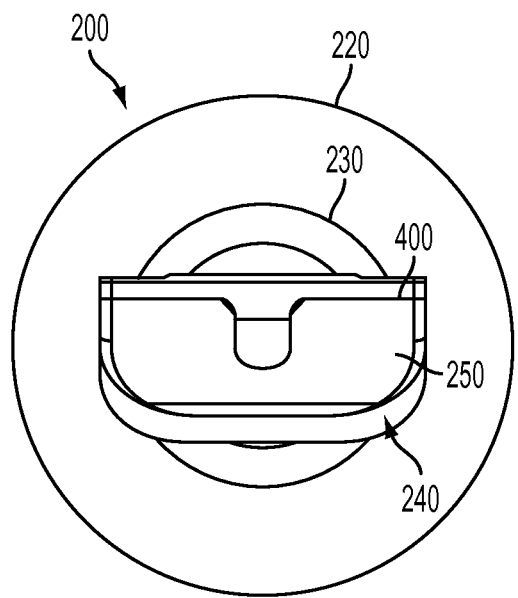
FIG. 7 is a detailed view of the distal end of a decorticating instrument, marked as "Detail B" on FIG. 5(b), according to various embodiments.

The inclined blade 250, as shown in FIG. 5(*c*) and, in more detail, in FIG. 7, may be tapered in overall shape from a first thickness toward the linear distal edge 400 to form a blade edge. The blade 250 may be inclined at an acute angle toward the medial face, relative to the longitudinal axis of the instrument 200, as shown in FIG. 5(b).

The inclined blade 250 may be positioned on the lateral face of the implement 500, as shown in FIG. 5(b). As shown, the inclined portion of the blade 250 may be generally rhomboidal in shape. Also, the blade 250 may extend from the tapered body 240, as shown, and may include one or more additional tapered surfaces, as shown in FIG. 5(c). In this aspect, the inclined blade 250 may appear to be generally wedge-shaped.

FIG. 7 is a detail, end view of the instrument 200. As shown, the tapered body 240 may have rounded edges; for example, having a radius of 0.100 inches. The blade 250, as shown, extends toward the linear distal edge 400 to form a blade edge. The detail view shows the shaft 230 and the proximal handle 220 of the implement 200. The blade edge, positioned along and coincident with the linear distal edge 400, may include a distal notch 420 near its center, as shown in FIG. 7 and in FIG. 6.

As described above, and illustrated in FIG. 5(b), the truncated scoop 260 also terminates along the distal edge 400. In this aspect, the scoop 260 and the blade 250 may cooperate during use, as described herein. For example, the blade 250 may be pushed in a lateral direction, away from the guide wire, along a bony surface, in order to selectively decorticate the bony surface. Then, the scoop 260 may be pulled in a medial direction, back toward the guide wire, along the bony surface, in order to further decorticate the bony surface. This back-and-forth motion may facilitate the selective decortication of a bony surface—with the guide wire serving as a tactile reference point for the user. For example, as the medial face of the scoop 260 travels back toward the guide wire, the semi-circular groove 280 and/or the distal notch 400 may partially engage with the guide wire, providing a tactile signal to the user when the implement 500 is positioned near the guide wire.

The instrument 100, in various embodiments, may be used in a method of selectively decorticating or otherwise preparing a surface, such as a bony surface, during a surgical procedure. For example, a bone fusion procedure may include the step of percutaneously accessing a desired motion segment of the spine. A motion segment generally comprises a first vertebral body and an adjacent second vertebral body.

The method of selectively decorticating a particular bony surface, in order to prepare it for service as a bone graft bed may include the steps of: (1) inserting a guide wire percutaneously and anchoring the guide wire near a selected bone graft bed; (2) sliding a decorticating instrument along the guide wire toward the bone graft bed; and (3) manipulating the decorticating instrument against the bone graft bed in order to selectively decorticate it.

Decortication, generally, is used herein to describe the process of abrading the surface of cortical bone. The abrasion may remove the periosteum, which is a membrane that lines the outer surface of most bones. The abrasion of decortication may also cause micro-trauma to the bone which, in certain applications, may provoke a fracture response. In other words, the bony surface and surrounding tissue may respond to decortication in a manner that is similar to the way it would respond to a bone fracture. In another aspect, decortication may be accomplished without de-vascularizing or otherwise traumatizing the blood vessels in the bone.

The instrument 100, described herein, may include an implement 300 having a semi-circular groove 180 along one of its sides or faces and/or a distal notch 220 positioned along a generally linear distal edge 200 of the instrument. To use the instrument, in particular embodiments, the groove 180 and/or the notch 220 may be placed against a portion of a guide wire such as Kirschner wire (K-wire) that lies outside the body. Once so engaged, the instrument 100 may be slid along the guide wire, into the body, and toward the bony surface where the guide wire 10 is anchored, as illustrated in FIG. 1. While sliding along the guide wire 10, the groove 180 and/or the notch 220, separately or together, provide tactile feedback to the user about the location of the instrument 100. For example, if the groove 180 and/or the notch 220 becomes disengaged from the guide wire 10, then the user will receive a tactile sensation that the instrument 100 is no longer sliding against the guide wire 10. In response, the user may manipulate the instrument 100 in various directions, including toward the guide wire 10, and re-engage the groove 180 and/or the notch 220 with the guide wire 10.

FIG. 1 illustrates the distal end of the instrument 100 positioned against the bony surface where the guide wire 10 is anchored. As shown, the truncated scoop 160 defines a generally semi-cylindrical groove 180 that is oriented generally parallel to the longitudinal axis of the instrument 100. The groove 180, in particular embodiments, may extend into and through a distal notch 220 located near the center of the linear distal edge 200 as shown.

Manipulation of the instrument against the bony surface may include a back-and-forth motion, along with motion in any other desired directions. For example, the blade 150 may be pushed in a lateral direction, away from the guide wire 10, in order to selectively decorticate the bony surface. Then, the scoop 160 may be pulled in a medial direction, back toward the guide wire 10, in order to further decorticate the bony surface. This back-and-forth motion may facilitate the selective decortication of a bony surface—with the guide wire 10 serving as a tactile reference point for the user. For example, as the medial face of the scoop 160 travels back toward the guide wire, the semi-circular groove 180 and/or the distal notch 200 may partially engage with the guide wire, providing a tactile signal to the user.

After decorticating or otherwise preparing a bony surface to act as a bone graft bed, the instrument 100 may be used to place bone graft material onto the prepared bone graft bed. For example, the truncated scoop 160, together with its semi-cylindrical groove 180, may be used to guide or otherwise assist in moving the bone graft material onto the prepared bone graft bed.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the following claims. Moreover, although specific terms are employed herein, as well as in the claims which follow, they are used only in a generic and descriptive sense, and not for the purposes of limiting the described invention, nor the claims which follow.

The invention claimed is:

1. An instrument for selectively decorticating a bony surface to prepare it for use as a bone graft bed, the instrument comprising:
   an elongate shaft having a proximal handle, a distal end, and a longitudinal axis;

a decorticating implement disposed upon the shaft, the implement having a medial face and a generally opposing lateral face, the implement comprising:
(a) a truncated scoop disposed on the medial face, the scoop comprising a generally shallow bowl terminating along a linear distal edge, the scoop defining a groove positioned substantially parallel to the longitudinal axis, wherein the groove is sized and shaped to releasably receive a guide wire wherein the truncated scoop may be manipulated medially, toward the guide wire, in order to further selectively decorticate a selected bony surface;
(b) an inclined blade disposed on the lateral face, the blade tapering in shape from a first thickness toward the linear distal edge to form a blade edge coincident with the linear distal edge wherein the inclined blade may be manipulated laterally, away from the guide wire, in order to selectively decorticate a selected bony surface wherein the blade edge may be manipulated in any direction in order to selectively decorticate a selected bony surface;
(c) a distal notch positioned near a center portion of the linear distal edge, wherein the notch is sized and shaped to releasably receive the guide wire; and
wherein the groove or the distal notch or the groove and the distal notch, when positioned to receive the guide wire, cooperate to provide tactile feedback about the location of the instrument relative to the guide wire to a hand of a user manipulating the instrument.

2. The instrument of claim 1, wherein the groove extends into and through the distal notch.

3. The instrument of claim 1, wherein the groove is positioned along the face of the truncated scoop.

4. The instrument of claim 1, further comprising a tapered body between the shaft and the implement.

5. The instrument of claim 1, wherein the groove is further sized and shaped to guide bone graft material along the truncated scoop toward a bone graft bed.

6. The instrument of claim 1, wherein the groove, when positioned to receive the guide wire, provides tactile feedback about the location of the instrument relative to the guide wire to a hand of a user manipulating the instrument.

7. The instrument of claim 1, wherein the distal notch, when positioned to receive the guide wire, provides tactile feedback about the location of the instrument relative to the guide wire to a hand of a user manipulating the instrument.

8. The instrument of claim 1, wherein the groove and the distal notch, when positioned to receive the guide wire, cooperate to provide tactile feedback about the location of the instrument relative to the guide wire to a hand of a user manipulating the instrument.

9. A method of selectively decorticating a bony surface in a bone fusion procedure that includes percutaneously accessing a desired motion segment of a patient's spine, wherein the desired motion segment comprises a first vertebral body and an adjacent second vertebral body, the method comprising the steps of:
inserting a guide wire percutaneously and anchoring the guide wire near the bony surface;
sliding a decorticating instrument along the guide wire toward the bony surface, wherein the instrument provides tactile feedback about the location of the instrument relative to the guide wire; and
manipulating the decorticating instrument against the bony surface in order to selectively decorticate it and otherwise prepare it for use as a bone graft bed;
providing a decorticating instrument that has a shaft extending lengthwise along a longitudinal axis from a proximal handle toward a distal end;
a decorticating implement disposed upon the shaft, the implement tapering in shape from a first thickness toward a blade edge, and the implement defining a semi-cylindrical groove positioned substantially parallel to the longitudinal axis, wherein the groove is sized and shaped to releasably receive the guide wire, wherein the decorticating implement has a medial face and a generally opposing lateral face, and wherein the implement has:
(a) a truncated scoop disposed on the medial face, the scoop comprising a generally shallow bowl terminating along a linear distal edge coincident with the blade edge, wherein the semi-cylindrical groove is positioned along the scoop; and
(b) an inclined blade disposed on the lateral face, the blade tapering in shape from a first thickness toward the linear distal edge to form the blade edge.

10. The method of claim 9, wherein the implement further comprises a distal notch positioned near a center portion of the linear distal edge, wherein the notch is sized and shaped to releasably receive the guide wire.

* * * * *